US00PP23650P3

(12) United States Plant Patent
Kardos

(10) Patent No.: US PP23,650 P3
(45) Date of Patent: Jun. 4, 2013

(54) ***LANTANA* PLANT NAMED 'SUNNY SIDE UP'**

(50) Latin Name: ***Lantana* sp.**
Varietal Denomination: Sunny Side Up

(75) Inventor: Josh Kardos, Watkinsville, GA (US)

(73) Assignee: Plant Introductions, Inc., Watkinsville, GA (US)

( * ) Notice: Subject to any disclaimer, the term of this patent is extended or adjusted under 35 U.S.C. 154(b) by 459 days.

(21) Appl. No.: 12/924,742

(22) Filed: Oct. 4, 2010

(65) Prior Publication Data

US 2012/0084892 P1 Apr. 5, 2012

(51) Int. Cl.
*A01H 5/00* (2006.01)

(52) U.S. Cl.
USPC ..... Plt./227

(58) Field of Classification Search ..... Plt./227
See application file for complete search history.

(56) References Cited

U.S. PATENT DOCUMENTS

PP19,548 P2 12/2008 Dirr
PP21,539 P3 11/2010 Griffith

OTHER PUBLICATIONS

Plant Introductions, Inc.8-page handout with pictures of new plants (including *Lantana* 'Sunny Side Up') given to wholesale growers Jun. 2010.
Page 13 of Plant Introductions, Inc. booklet showing *Lantana* hybrids (including 'Sunny Side Up') as printed Dec. 31, 2009, distributed at tradeshows and by mail in 2010.
Plant Introductions, Inc. poster showing new plants (including *Lantana* 'Sunny Side Up') as displayed Feb. 17, 2010 at Pike Nurseries Employee Knowledge Fair.
Print out of slide of *Lantana* 'Sunny Side Up' used in a presentation Sep. 1, 2010 to wholesale growers.

*Primary Examiner* — June Hwu
*Assistant Examiner* — Louanne Krawczewicz Myers
(74) *Attorney, Agent, or Firm* — Lathrop & Gage LLP

(57) ABSTRACT

A new and distinct cultivar of *Lantana* plant named 'Sunny Side Up', characterized by its low growing, spreading growth habit; leathery, scabrous dark green foliage; continuous flowering; and yellow flower buds that open to yellow with a darker golden-yellow center and age to white with a yellow center.

2 Drawing Sheets

Genus and species of plant claimed: *Lantana* sp.
Variety denomination: 'Sunny Side Up'.

BACKGROUND OF THE INVENTION

The present invention relates to a new and distinct cultivar of *Lantana* plant, botanically known as *Lantana* sp., and hereinafter referred to by the cultivar name 'Sunny Side Up'.

The new *Lantana* plant originated from a controlled cross between *Lantana* sp. 'Chapel Hill Gold' (U.S. Plant Pat. No. 21,539) and an unnamed selection of *Lantana camara* (not patented) as part of a planned breeding program to develop low growing, continuously flowering *Lantanas* with dark green foliage. The cultivar 'Sunny Side Up' originated and was discovered in a cultivated environment in Watkinsville, Ga.

Asexual reproduction of the new cultivar by stem cuttings in Watkinsville, Ga. has shown that all the unique features of this new *Lantana*, as herein described, are stable and reproduced true-to-type through successive generations of such asexual propagation.

SUMMARY OF THE INVENTION

Plants of the new cultivar 'Sunny Side Up' have not been observed under all possible environmental conditions. The phenotype may vary somewhat with changes in light, temperature, soil and rainfall without, however, any variance in genotype.

The following traits have been repeatedly observed and are determined to be unique characteristics of 'Sunny Side Up'. These characteristics in combination distinguish 'Sunny Side Up' as a new and distinct cultivar: 1. Low growing, spreading growth habit; 2. Leathery, scabrous dark green foliage; 3. Continuous flowering; and 4. Yellow flower buds that open to yellow with a darker golden-yellow center and age to white with a yellow center.

Plants of the new *Lantana* 'Sunny Side Up' differ from plants of the female parent, 'Chapel Hill Gold', primarily in flower color, as plants of 'Chapel Hill Gold' have bright golden yellow flower buds and flowers, whereas plants of 'Sunny Side Up' have yellow flower buds that open to yellow with a darker golden-yellow center and age to white with a yellow center. Plants of the new *Lantana* 'Sunny Side Up' differ from plants of the male parent, an unnamed selection, primarily in flower color, foliage color, and growth habit, as plants of the male parent have white flower buds that open to solid white flowers, medium green foliage, and a smaller, rounded growth habit, whereas plants of 'Sunny Side Up' have yellow flower buds that open to yellow with a darker golden-yellow center and age to white with a yellow center, dark green foliage, and an overall wider, lower, spreading growth habit.

Plants of the new cultivar 'Sunny Side Up' can be compared to plants of the cultivar 'LCBCW' (not patented). However, in side-by-side comparisons conducted in Watkinsville, Ga., plants of the new cultivar 'Sunny Side Up' differed from plants of the cultivar 'LCBCW' in the following characteristics: 1. Plants of the new cultivar 'Sunny Side Up' had darker green, thicker, more scabrous foliage than plants of the cultivar 'LCBCW'; 2. Plants of the new cultivar 'Sunny Side Up' had brighter flower color and larger flowers than plants of the cultivar 'LCBCW'; and 3. Plants of the new cultivar 'Sunny Side Up' produced a finished size saleable plant quicker than plants of the cultivar 'LCBCW'.

BRIEF DESCRIPTION OF THE DRAWINGS

The accompanying color photographs illustrate the flower and foliage characteristics and the overall appearance of the new *Lantana*, showing the colors as true as it is reasonably possible to obtain in color reproductions of this type. Colors in the photographs may differ slightly from the color values cited in the detailed botanical description which accurately describe the colors of the new *Lantana*.

DETAILED DESCRIPTION

Figure 1:
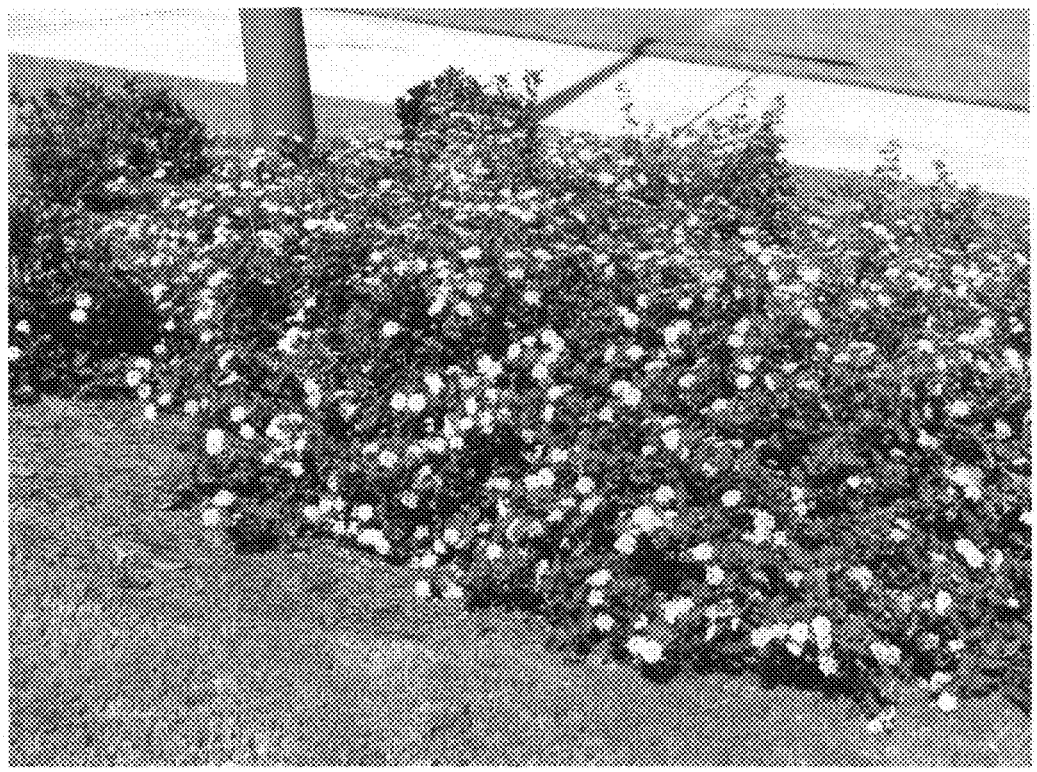
FIG. 1 illustrates the overall appearance of a mature plant of 'Sunny Side Up'.
Figure 2:
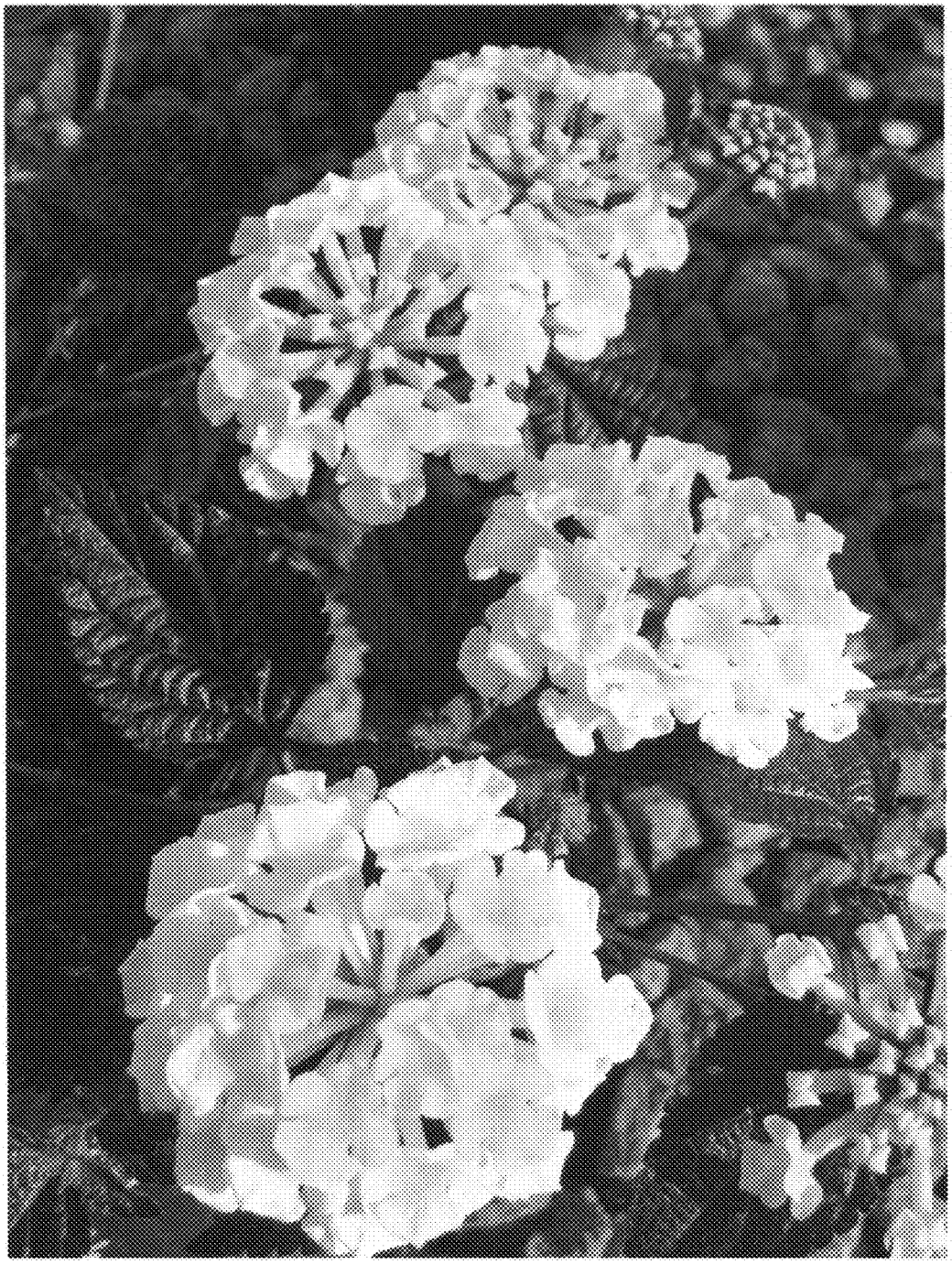
FIG. 2 illustrates a close-up view of the inflorescences and foliage of 'Sunny Side Up'.

In the following description, color references are made to The Royal Horticultural Society Colour Chart, 2001 Edition, except where general terms of ordinary dictionary significance are used. Plants used for the description were approximately six months old and were grown in 8 L containers in full sun under outdoor conditions in a nursery in Watkinsville, Ga.

Botanical classification: *Lantana* sp., cultivar 'Sunny Side Up'.

*Parentage*.—Female parent: *Lantana* sp. cultivar 'Chapel Hill Gold' (U.S. Plant Pat. No. 21,539). Male parent: *Lantana camara* unnamed selection (not patented).

*Propagation*.—Stem cuttings.

*Time to initiate roots, summer*.—About 10 days at 32° C.

Plant description:

*Herbaceous flowering plant, subshrub, low growing, spreading growth habit*.—Freely branching; two lateral branches potentially forming at every node; pinching enhances lateral branch development.

*Root description*.—Numerous, fine, fibrous and well-branched.

*Plant size*.—About 45 cm in height from the soil level to the top of the inflorescences, and about 120 cm in diameter. Young stems having a diameter of about 3 mm and a squarish shape. Mature stems having a diameter of about 4 mm or more, having a length of 58 cm, and a rounded shape.

*Stem strength*.—Strong, but flexible.

*Stem texture*.—Coarse, pubescent.

*Stem color* (*young*).—144B. Color (mature): 199B.

*Internode length*.—About 3.5 cm.

Vegetative buds: Opposite in arrangement, valvate, ovoid, pubescent.

*Color*.—144A.

*Size*.—About 1 mm in length and about 1 mm in width.

Foliage description:

*Arrangement*.—Opposite, simple. Length: about 4 cm. Width: about 2.7 cm. Shape: ovate. Apex: acute. Base: cuneate. Margin: crenate.

*Texture* (*upper surface*).—Leathery, moderately waxy, with scabrous pubescence. Texture (lower surface): rough, with hispid pubescence.

*Venation pattern*.—Pinnate. Venation color (upper surface): 144B. Venation color (lower surface): 144C.

*Fragrance*.—Pungent, mint-like.

*Color of developing foliage* (*upper surface*).—137B. Color of developing foliage (lower surface): 143C. Color of fully expanded foliage (upper surface): 147A. Color of fully expanded foliage (lower surface): 147B.

*Petiole length*.—About 7 mm. Petiole diameter: about 2 mm. Petiole texture, both surfaces: hispid pubescence. Petiole color (upper surface): 144B. Petiole color (lower surface): 144C.

Flower description:

*Flower type and habit*.—Small salverform flowers arranged in axillary corymbs; flowers face mostly upward or outward. Flowers are self-cleaning. Freely flowering with potentially two inflorescences per node; typically about 25 flowers per corymb. Natural flowering season: spring until the first frost in fall; flowering is continuous. Flower longevity on the plant: about one week. Fragrance: faint, pleasant.

*Inflorescence diameter*.—About 3.9 cm. Inflorescence height: about 2 cm.

*Flower bud length*.—About 1 cm. Flower bud diameter: about 3 mm. Flower bud shape: oblong. Flower bud color: 12C.

*Flower appearance*.—Flared trumpet, corolla fused, four-parted; flowers roughly rectangular in shape. Floret diameter: about 1.1 cm. Floret depth: 1.1 cm. Corolla tube diameter at the base: 2 mm. Corolla tube length: about 1.3 cm.

*Pedicels*.—None observed, flowers not stalked.

Petals:

*Arrangement/appearance*.—Single whorl of four petals, fused into flared trumpet.

*Petal length from throat*.—About 7 mm for the upper petal, about 5 mm for the lower petal, and about 4.5 mm for the lateral petals.

*Petal width*.—Upper and lower petals are about 8 mm in width, and lateral petals are about 5 mm in width.

*Petal shape*.—Spatulate to somewhat orbicular. Petal apex: obtuse. Petal base: fused. Petal margin: entire. Petal texture, upper and lower surfaces: smooth, glabrous.

*Petal color* (*young*).—Upper surface: 4C and lower surface: 4D. Color of throat: 13A. Color of corolla tube: 8C.

*Petal color* (*mature*).—Upper and lower surfaces: 155C. Color of throat: 9A. Color of corolla tube: 8D.

Calyx:

*Arrangement/appearance*.—Leaf-like at the base of the corolla. Length is about 6 mm. Width is about 1.5 mm. Shape: lanceolate. Apex: acute. Margin: entire. Texture, upper and lower surface: scabrous.

*Calyx color, upper and lower surfaces*.—144A.

Peduncles:

*Length*.—About 5 cm.

*Diameter*.—About 1.5 mm.

*Angle*.—About 45 degrees from the stem.

*Strength*.—Flexible, but strong.

*Color*.—144B.

Stamens:

*Quantity/arrangement*.—Four per flower, adnate to the inside of the corolla tube.

*Anther shape*.—Oblong.

*Filament length.*—1.5 mm.
*Anther length.*—1 mm.
*Anther width.*—Less than 1 mm.
*Anther color.*—13B.
*Pollen amount.*—Produced in very small quantities, and 13B in color.

Pistils:
*Quantity.*—One inferior pistil per flower.
*Pistil length.*—About 3 mm.
*Stigma shape.*—Rounded.
*Stigma color.*—145C.
*Style color.*—145C.
*Ovary color.*—145C.

Fruit:
*Type/appearance.*—Drupe.
*Shape.*—Round.
*Diameter.*—About 5 mm.
*Mature color.*—202A.
*Number per infructescence.*—Ranges from zero to about five.

Disease/pest resistance: Plants of the claimed *Lantana* variety grown in the garden have not been noted to be susceptible or resistant to pathogens and pests common to *Lantana*.

Weather and temperature tolerance: Plants of the new *Lantana* cultivar have been observed to be tolerant to rain and wind, and have been observed to be tolerant to temperatures ranging from about 2 degrees C. to about 38 degrees C.

I claim:

1. A new and distinct *Lantana* plant named 'Sunny Side Up', as illustrated and described herein.

* * * * *